(12) United States Patent
Bills

(10) Patent No.: US 7,169,134 B2
(45) Date of Patent: Jan. 30, 2007

(54) APPARATUS WITH ROTATABLE VALVE SYRINGE

(75) Inventor: Dan J. Bills, Salt Lake City, UT (US)

(73) Assignee: Ultradent Products, Inc., South Jordan, UT (US)

( * ) Notice: Subject to any disclaimer, the term of this patent is extended or adjusted under 35 U.S.C. 154(b) by 787 days.

(21) Appl. No.: 10/106,397

(22) Filed: Mar. 26, 2002

(65) Prior Publication Data

US 2003/0187407 A1   Oct. 2, 2003

(51) Int. Cl.
  *A61M 5/315* (2006.01)
(52) U.S. Cl. .................. 604/236; 604/241; 604/111
(58) Field of Classification Search ........ 604/236–238, 604/187, 110–111, 275, 279, 192, 218, 239, 604/263, 82, 83, 181, 207, 240–243, 246, 604/248, 256, 177; 222/386, 387; 433/28, 433/80, 89–90, 82, 87
See application file for complete search history.

(56) References Cited

U.S. PATENT DOCUMENTS

| | | | |
|---|---|---|---|
| 1,831,668 A | 11/1931 | Juhl | |
| 2,261,213 A | 11/1941 | Bierman | 128/214 |
| 3,277,922 A | 10/1966 | Eisel | 137/613 |
| 4,043,336 A | 8/1977 | Kreb, III | 128/218 R |
| 4,175,559 A * | 11/1979 | Kreb, III | 604/199 |
| 4,679,705 A | 7/1987 | Hamilton | 222/90 |
| 4,758,158 A * | 7/1988 | Pierce et al. | 433/90 |
| 4,834,706 A * | 5/1989 | Beck et al. | 604/111 |
| 4,846,801 A | 7/1989 | Okuda | 604/218 |
| 4,929,232 A * | 5/1990 | Sweeney et al. | 604/111 |
| 4,931,044 A | 6/1990 | Beiter | 604/248 |
| 5,135,511 A | 8/1992 | Houghton | 604/220 |
| 5,178,186 A | 1/1993 | Lavsseur | 137/556 |
| 5,286,257 A * | 2/1994 | Fischer | 604/82 |
| 5,814,017 A | 9/1998 | Kashmer | 604/110 |
| 5,816,804 A * | 10/1998 | Fischer | 433/90 |
| 5,944,698 A * | 8/1999 | Fischer et al. | 604/236 |
| 5,951,160 A | 9/1999 | Ronk | 366/130 |
| 5,989,219 A | 11/1999 | Villas | 604/110 |

* cited by examiner

*Primary Examiner*—Nicholas Lucchesi
*Assistant Examiner*—Theodore J. Stigell
(74) *Attorney, Agent, or Firm*—Workman Nydegger

(57) ABSTRACT

Valve syringes of the invention include a barrel, a plunger and an applicator valve. The applicator valve, which controls the flow of the fluid material contained within the barrel, can rotate at the end of the barrel between an open position and a closed position. In the open position, slots in the applicator valve align with holes in the barrel and allow the fluid material to flow therethrough. In the closed position, a contact surface seals the holes in the barrel closed to prevent the flow of the fluid material therethrough. The applicator valve includes an applicator tip that is either integrally connected to or detachably connected with the applicator valve. The valve syringe also includes means for releasably securing the applicator valve in the closed position to prevent undesired leaking and evaporation during periods of nonuse.

20 Claims, 10 Drawing Sheets

APPARATUS WITH ROTATABLE VALVE SYRINGE

BACKGROUND OF THE INVENTION

1. The Field of the Invention

The present invention is in the field of dental composition delivery systems and, more particularly, in the field of dental syringes.

2. The Relevant Technology

In the field of dentistry, dental compositions are often delivered through a syringe. While some syringes contain only enough composition for a single application, other syringes contain enough composition to be used a plurality of times on a single patient or on a plurality of patients.

One benefit of multi-dose syringes, over the single dose syringes, is that they are generally more cost efficient. One drawback of multi-dose syringes, however, is that they are susceptible to cross-contamination. Another drawback includes the difficulty of ensuring the syringe is properly sealed between uses to prevent undesired leakage and evaporation or premature curing of the composition within the syringe. For instance, the tips of existing syringes are typically sealed closed with threaded or friction fitting caps. However, there is a risk the closure caps will not be sufficiently tightened onto the tips of the syringes between uses because the existing syringes do not include means for indicating when the caps are sufficiently sealed or tightened onto the tips of the syringes. Yet another problem with multi-dose syringes is that the syringe caps or lids can easily be misplaced or lost, thereby preventing the syringes from being adequately sealed. When the cap is not sufficiently sealed on the tip of a syringe then the composition within the syringe can leak, evaporate, or prematurely cure, thereby minimizing the cost advantage of purchasing the larger capacity multi-dose syringes.

Single dose syringes provide an improvement over the multiple dose syringes for at least minimizing any risk of cross-contamination. However, single dose syringes are also susceptible to undesired leakage and evaporation or premature curing of the dental composition contained therein. In particular, the closure caps placed over the tips of existing single dose syringes can become dislodged during shipping, storage, and other periods of nonuse, thereby enabling the composition to leak or evaporate.

Accordingly, in view of the foregoing, there is currently a need in the art for improved syringe delivery systems and, more particularly, to syringe delivery systems that that are configured to reduce leakage and evaporation, or premature curing during shipping, storage, and other periods of nonuse.

SUMMARY OF PRESENTLY PREFERRED EMBODIMENTS

Briefly summarized, presently preferred embodiments of the present invention are directed to improved syringe delivery systems.

According to one presently preferred embodiment, the valve syringe of the invention includes a barrel configured for containing a fluid material, a plunger configured for pushing the fluid material to an outlet end of the barrel, and an applicator valve disposed at the outlet end of the barrel that is also configured to rotate between an open position and a closed position for controlling the flow of the fluid material through the applicator valve.

The applicator valve also includes an internal contact surface configured to frictionally engage the tapered outlet end of the barrel for preventing the fluid material from flowing through the opening formed in the outlet end of the barrel when the applicator valve is in the closed position during periods of nonuse. The applicator valve also includes at least one relief slot formed in the internal contact surface that is configured to allow the fluid material to flow through the barrel opening when the applicator valve is in the open position during use. When the applicator valve is in the open position, the fluid material is able to flow through the applicator valve and into an applicator tip through which the fluid material is dispensed.

The applicator tip, which is specifically configured to dispense the composition contained in the barrel of the syringe, comprises at least one of a cannula, a needle, a curved hollow body, and a flocked applicator tip. In one embodiment, the applicator tip is integrally connected to the applicator valve. In another embodiment, the applicator tip is detachably coupled with the applicator valve, such as with threaded surfaces or other coupling means.

The valve syringe further includes securing means for releasably securing the applicator valve in the closed position during periods of nonuse. Securing means are useful for helping to prevent inadvertent rotation of the applicator valve into the open position during shipping, storage, and other periods of nonuse. Securing means may include any engagement formation configured to frictionally resist rotation of the applicator valve from the closed position. In one embodiment, the securing means includes knobs and recesses, wherein the knobs are configured to mate within the recesses only when the applicator valve is in the closed position, thereby resisting rotation of the applicator valve from the closed position.

The applicator valve may also include rotation facilitating means for facilitating rotation of the applicator valve between the open and closed positions, notwithstanding the presence of any securing means. In one embodiment, the rotation facilitating means includes protruding wing members extending from the applicator valve. The protruding wing members are specifically configured to be engaged by the fingers of a user and generally increase the leverage that can be applied for rotating the applicator valve. To prevent over-rotation of the applicator valve, the valve syringes also include stopping means for stopping rotation of the applicator valve in the open position when the applicator valve is rotated in a first direction and for stopping rotation of the applicator valve in the closed position when the applicator valve is rotated in the opposite direction. According to one embodiment, the stopping means includes at least one radial block member protruding away from the applicator valve and configured to engage the tab members once the applicator valve is completely rotated into either one of the open and closed positions.

The applicator valve is secured on the end of the syringe by retaining means which, according to one embodiment, includes a ridge member circumferentially extending at least partially around the applicator valve and at least one tab member extending from the barrel. The tab members slidably engage the at least one ridge member while the applicator valve is rotated between the open and closed positions, thereby retaining the applicator valve on the syringe.

According to one embodiment the valve syringe also includes tamper evident means for indicating whether the applicator valve has rotated from the closed position to the open position at least one time. The tamper evident means may include a flange, a bridge, or any other physical coupling between the applicator valve and the barrel of the syringe. When the applicator valve is rotated from the closed position to the open position for the first time then the tamper evident means is visually and irreversibly broken.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

A detailed description of the valve syringe of the invention will now be provided with specific reference to figures illustrating preferred embodiments of the invention. It will be appreciated that like structures will be provided with like reference designations.

In order to provide context for interpreting the scope of the invention, certain terms will now be defined. The term "composition," as used herein, refers to any fluid material or fluid composition of materials capable of being dispensed through a syringe. By way of example and not limitation, the compositions referred to herein include organic and synthetic compositions as water and solvent based compositions. Although the terms "composition" and "fluid material" are used interchangeably herein, it will be appreciated that the compositions and fluid materials are not limited to having any particular viscosity. Rather the viscosity of the fluid materials can vary to accommodate different needs and preferences, but should be at least low enough to flow through the applicator valve and applicator tip during normal use.

The term "applicator tip," as defined herein, refers to any tip, tube, needle, cannula, and other dispensing device configured to dispense a fluid material and is characterized by the attribute of including at least a hollow or concave portion through which the fluid material can flow.

The term "luer taper," as used herein, refers to a standard luer taper of about six degrees (6%) as described in document "ISO 594-2: 1998 Conical fittings with 6% (Luer) taper for syringes, needles and certain other medical equipment—Part 2: Lock fittings." However, it will be appreciated that the luer taper may also comprise other angles that are either less than or greater than six percent as desired.

The term "mating engagement formations," as defined herein, refers to any combination of engaging formations, including, but not limited to, recesses, ridges, protrusions, holes, latches, clips, knobs, pins, slots, tabs, and apertures which are configured to interconnect, internest, mate, lock, or otherwise frictionally engage.

The valve syringes of the invention, as described herein, are generally configured to control the flow of fluid material through an application valve disposed at the outlet end of a syringe barrel. During use, fluid material flowing through the application valve is dispensed through an application tip, which is either integrally connected to or detachably connected with the applicator valve.

Figure 1:
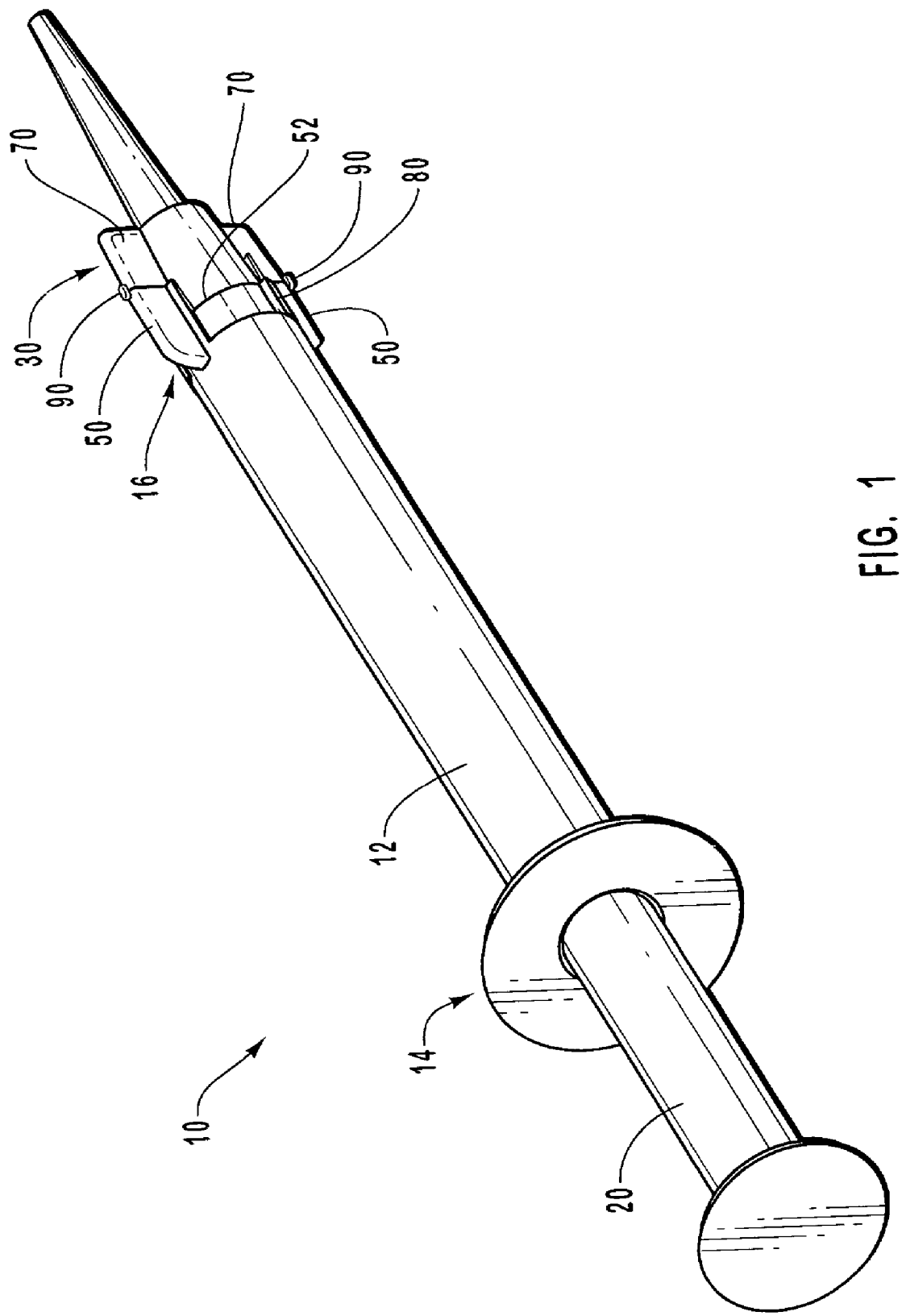
FIG. 1 illustrates a back perspective view of one embodiment of the valve syringe of the invention that includes a barrel configured for containing a fluid material, a plunger configured for pushing the fluid material to the outlet end of the barrel, and an applicator valve disposed at the outlet end of the barrel.

FIG. 1 illustrates one presently preferred embodiment of the valve syringe 10 of the invention. As shown, the valve syringe 10 generally includes a barrel 12 configured for containing a fluid material. The barrel 12 has a generally cylindrical cross-sectional shape and extends from an inlet end 14 to an outlet end 16. It will be appreciated that the cross-sectional shape of the barrel 12 may vary to accommodate various needs and preferences. The plunger 20, inserted within the inlet end 14 of the barrel 12, is specifically configured in shape and size for pushing the fluid material contained within the barrel 12 to the outlet end 16 of the barrel 12, where it is forced through and dispensed out of the applicator valve 30. The applicator valve 30 is preferably configured in size and shape for rotatably engaging the outlet end 16 of the barrel 12.

Figure 2:
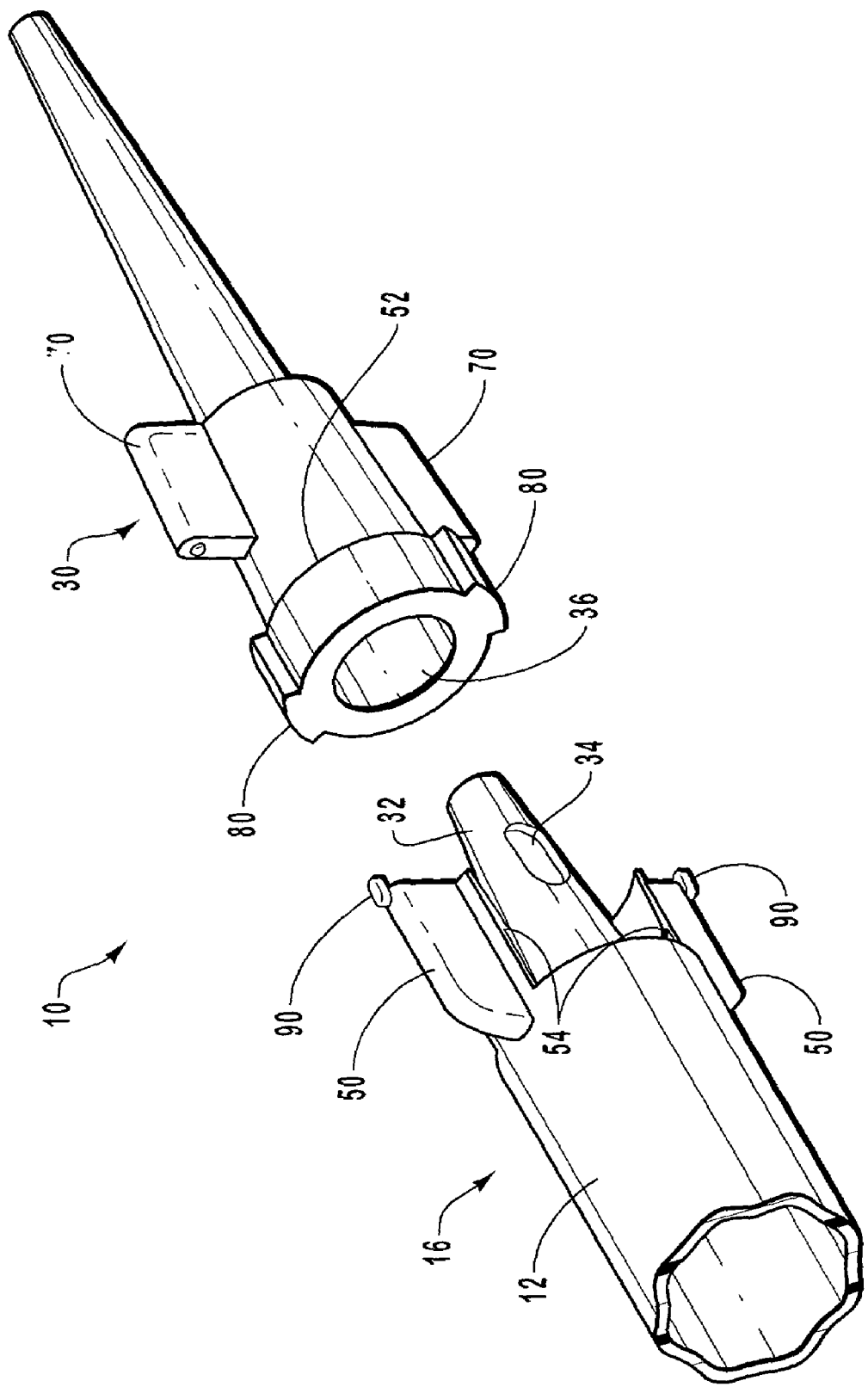
FIG. 2 illustrates an exploded perspective view of the outlet end of the barrel and the applicator valve.

FIG. 2 illustrates an exploded view of the applicator valve 30 and the outlet end 16 of the barrel 12. As shown, the outlet end 16 of the barrel 12 includes a sidewall 32 with at least one barrel opening 34 formed in the sidewall 32. The sidewall 32 is preferably tapered, such as with a standard 6% luer taper. It will be appreciated, however that the angle of the taper may vary to accommodate different needs and preferences.

According to one present embodiment, the valve syringe 10 includes two barrel openings 34 that are disposed in opposite sides of the sidewall 32, although only one of the barrel openings 34 can be seen in the illustration shown.

According to the preferred embodiment, the applicator valve 30 also includes a contact surface 36 that is correspondingly tapered to abuttingly engage the outlet end 16 of the barrel 12. In particular, the contact surface 36 of the applicator valve 30 is configured in size and shape to engage the sidewall 32 of the outlet end 16 of the barrel 12 so as to prevent the fluid material from exiting through the barrel openings 34 when the applicator valve 30 is disposed in a closed position, as generally shown and described below in reference to FIG. 3.

Figure 3:
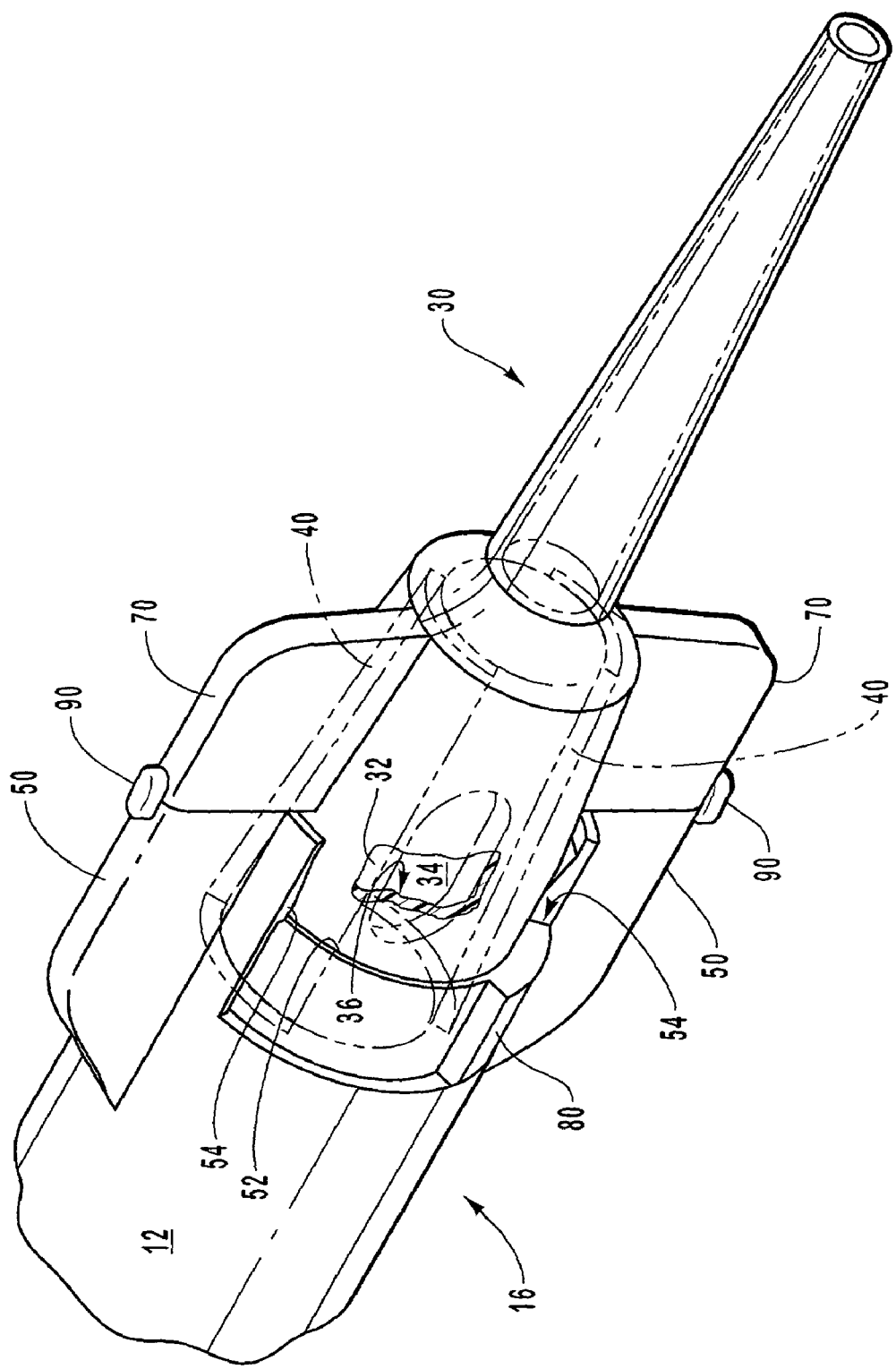
FIG. 3 illustrates a partial cross-sectional perspective view of the outlet end of the barrel and the applicator valve with the applicator valve disposed in the closed rotational position.

FIG. 3 illustrates a partial cross-sectional perspective view of the applicator valve 30 disposed on the outlet end 16 of the barrel 12 in a closed position. As shown, in the closed position, the contact surface 36 of the applicator valve 30 covers the barrel opening 34 to prevent the fluid material from passing therethrough.

Figure 4:
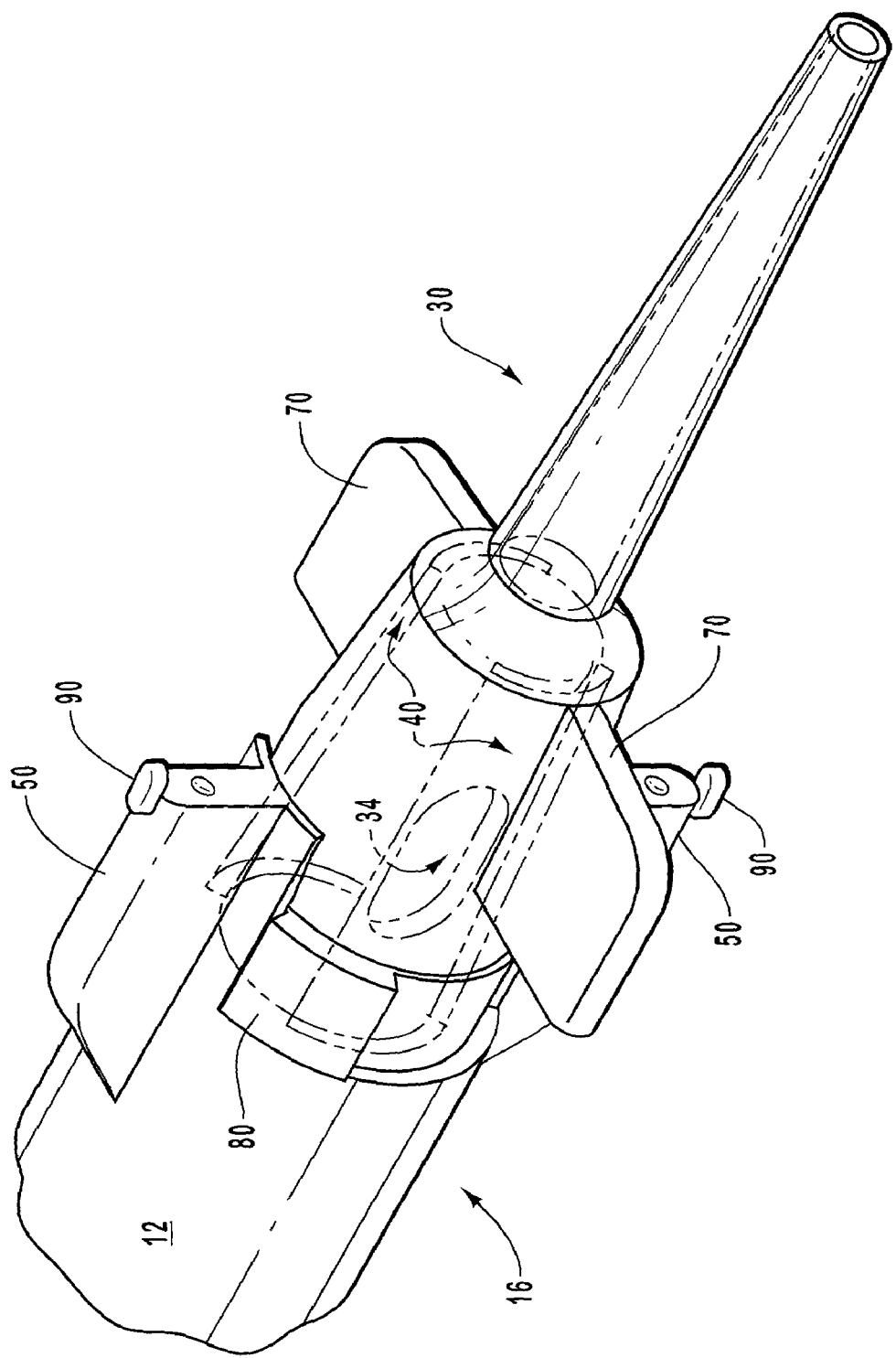
FIG. 4 illustrates a front perspective view of the outlet end of the barrel and the applicator valve with the applicator valve disposed in the open rotational position.

FIG. 4 illustrates the applicator valve 30 in an open position. As shown, relief slots 40 formed within the contact surface of the applicator valve 30 at least partially align with the barrel openings 34 in the outlet end 16 of the barrel 12, although only one barrel opening 34 is presently visible in this view. This arrangement of the relief slots 40 and the barrel openings 34 is further clarified by the illustration shown in FIG. 5.

Figure 5:
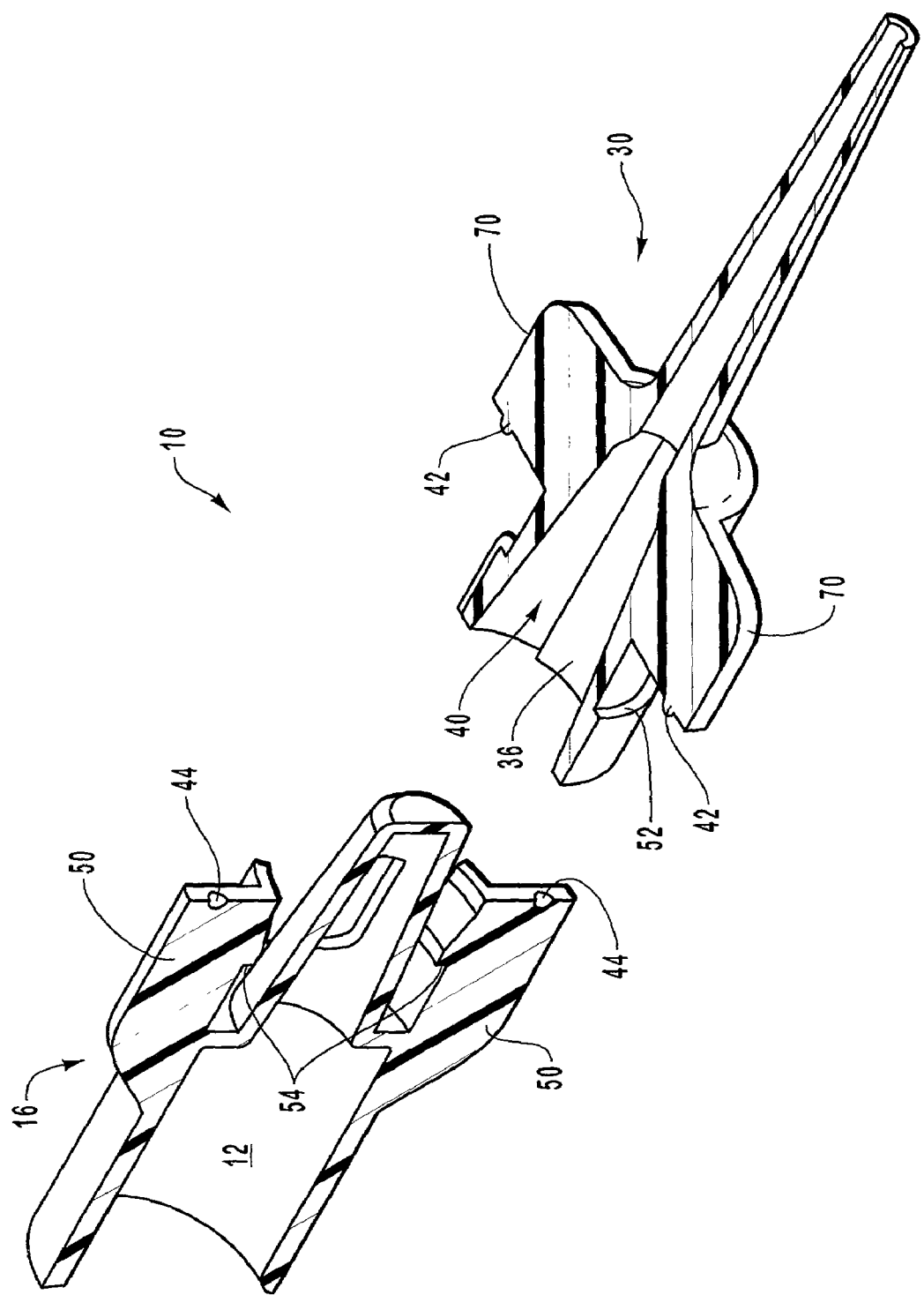
FIG. 5 illustrates a cross-sectional exploded view of the outlet end of the barrel and the application valve that also shows the alignment of the barrel opening and the relief slot when the application valve is rotationally aligned in the open position.

FIG. 5 illustrates an exploded cross-sectional view of the outlet end 16 of the barrel 12 and of the applicator valve 30. As shown, the applicator valve 30 is concentrically aligned with the barrel 12 and rotated with respect to the barrel in the rotational alignment of the open position shown in FIG. 4. It is evident that when the applicator valve 30 is disposed on barrel 12 in this rotational alignment, within an open position, that the barrel opening 34 at least partially aligns with the relief slot 40 formed into the contact surface 36 of the applicator valve 30. It should also be appreciated that by aligning the barrel opening 34 with the relief slots, in the open position, that the composition within the barrel will be able to flow through the barrel openings 34 and into the applicator valve through which it is dispensed during use. Flow can occur even when the openings are only partially aligned, although some restriction may occur depending on the degree of alignment.

FIG. 5 also illustrates securing means for releasably securing the applicator valve 30 in the closed position. In particular, knobs 42 and recesses 44 formed in the valve syringe 10 are configured to internest in mechanical engagement when the applicator valve 30 is disposed in the fully closed position, which is shown and described above in reference to FIG. 3. The securing means may also include any other combination of mating engagement formations, including, but not limited to, recesses, ridges, protrusions, holes, latches, clips, knobs, pins, slots, tabs, and apertures which are configured to interconnect, internest, mate, lock, or otherwise mechanically or frictionally engage when the applicator valve 30 is in the closed position.

It will be appreciated that the securing means of the invention are useful for at least enabling a user to know when the applicator valve 30 is completely rotated into the closed position. In this manner, the valve syringes 10 of the invention provide an improvement over prior art devices which include closure caps that do not have any means for indicating when the cap is sufficiently placed over the syringe to prevent the flow or evaporation of the fluid material contained therein. Instead, prior art devices require the user to repeatedly determine how tightly the closure cap must be placed on the syringe to prevent undesired leaking and evaporation of the fluid material contained within the syringe. In contrast, the securing means of the present invention enable a user to know exactly how far the applicator valve 30 must be rotated to secure the applicator valve 30 in the closed position. Once in the closed position, the securing means also prevent the applicator valve 30 from being inadvertently rotated into the open position. In this manner the securing means of the invention also provide an improvement over prior art devices that include closure caps that can easily become dislodged or unsecured during shipping, storage, and other periods of nonuse.

FIGS. 1–5 also illustrate retaining means for retaining the applicator valve 30 on the outlet end 16 of the barrel 12. In these presently shown embodiments, the retaining means includes tab members 50 extending from the outlet end 16 of the barrel 12 and a ridge member 52 circumferentially extending at least partially around the applicator valve 30. As shown, each of the tab members 50 includes a ledge 54 configured to slidably engage the ridge member 52 of the applicator valve 30 during rotation of the applicator valve 30 between the open and closed positions. In this manner the valve syringe 10 of the invention provides means for retaining the applicator valve 30 at the outlet end 16 of the barrel 12. It will be appreciated, however, that the applicator valve 30 can still be removed from the outlet end 16 of the barrel 12 by flexing the tab members 50 away from the barrel 12 until the ledges 54 clear the ridge member 52. This is useful, for instance, to enable the applicator valve 30 to be interchanged. It may be desirable to interchange the applicator valve 30 when the sanitation of the applicator valve 30 is compromised, such as may occur when the valve syringe 10 is dropped on the floor, for instance.

Figure 6:
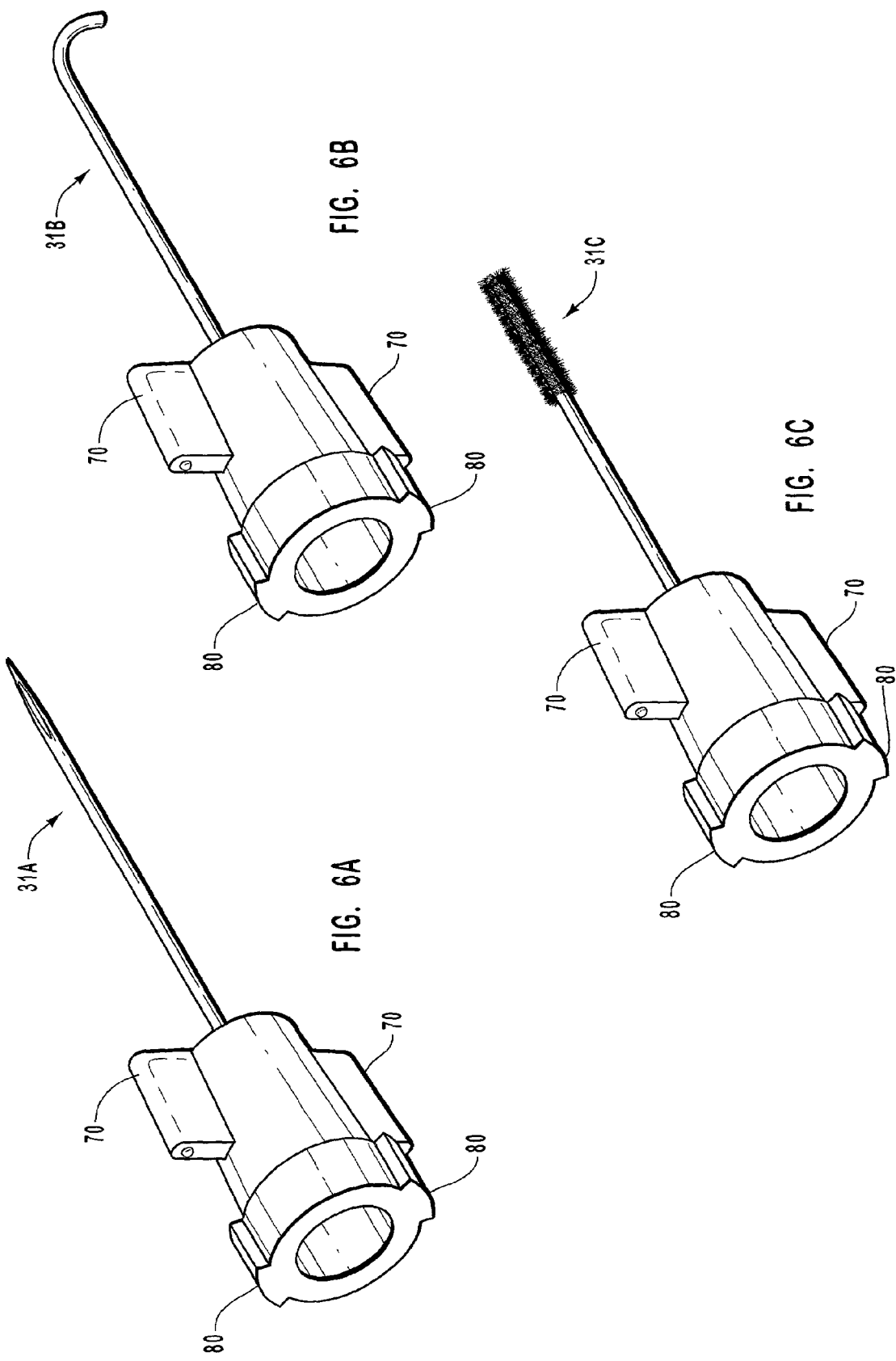
FIG. 6A illustrates a perspective view of one embodiment of the applicator valve of the invention that includes an applicator tip configured as a needle.
FIG. 6B illustrates a perspective view of one embodiment of the applicator valve of the invention that includes an applicator tip configured as a curved cannula.
FIG. 6C illustrates a perspective view of one embodiment of the applicator valve of the invention that includes a flocked applicator tip.

Although the barrel 12 of the valve syringe 10 can be configured for containing only enough composition for a single use, it can also be configured with a sufficiently large barrel 12 to contain multiple doses of the composition, in which case it is also desirable to interchange the applicator valve 30 between uses on different patients. It may also be desirable to interchange the applicator tip between uses on a single patient if the composition has mixed and cured within the applicator tip. Yet another reason to interchange the applicator valve 30 is to utilize the special attributes of differently shaped and configured applicator tips. For instance, the applicator tip may be configured as a needle applicator 31A, as a cannula applicator 31B, or as a flocked applicator 31C, as shown in FIGS. 6A–6C to accommodate different needs and preferences.

Figure 7:
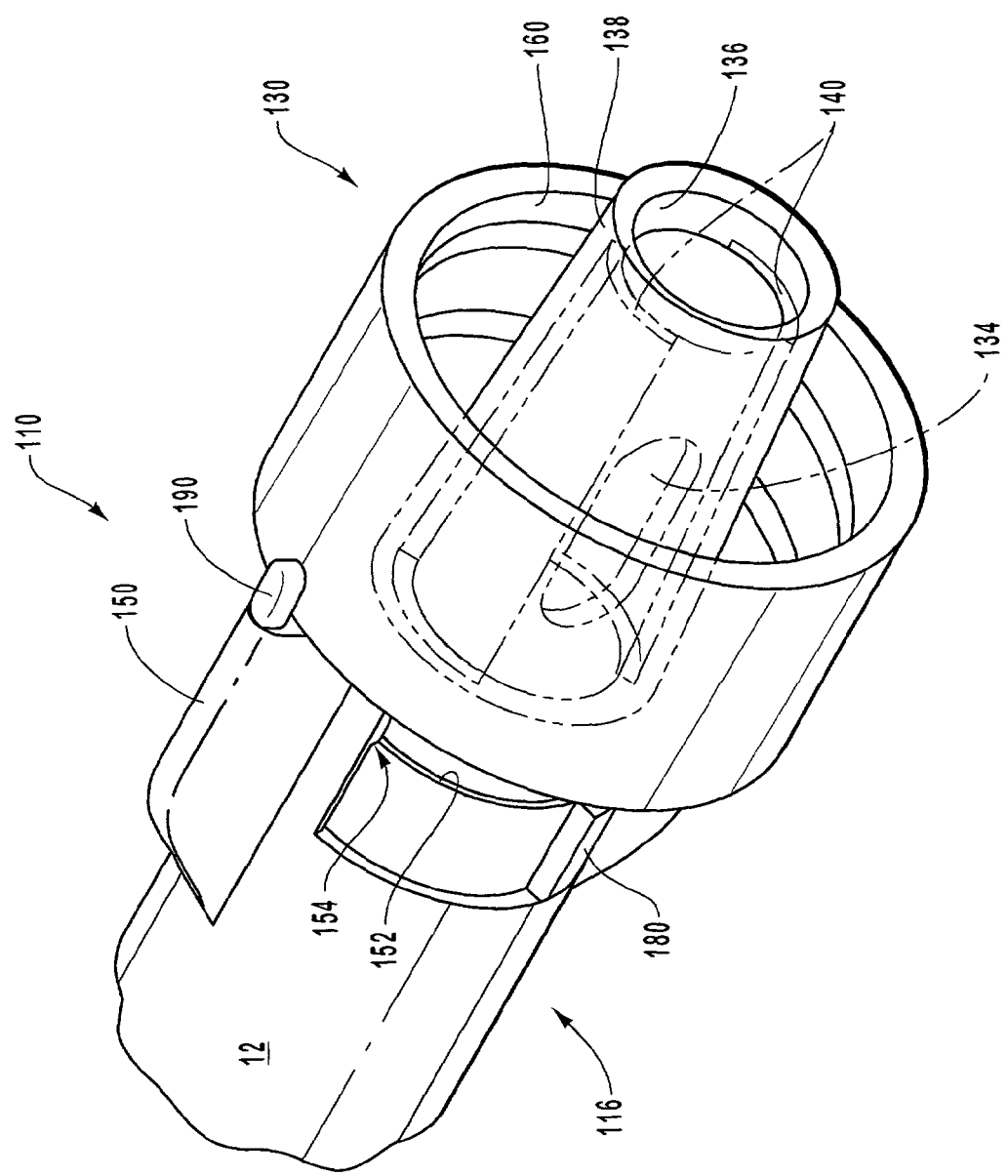
FIG. 7 illustrates one embodiment of the applicator valve of the invention that is disposed at the outlet end of the syringe barrel in a closed rotational position and which includes threaded coupling means for coupling the applicator valve to a threaded applicator tip.
Figure 8:
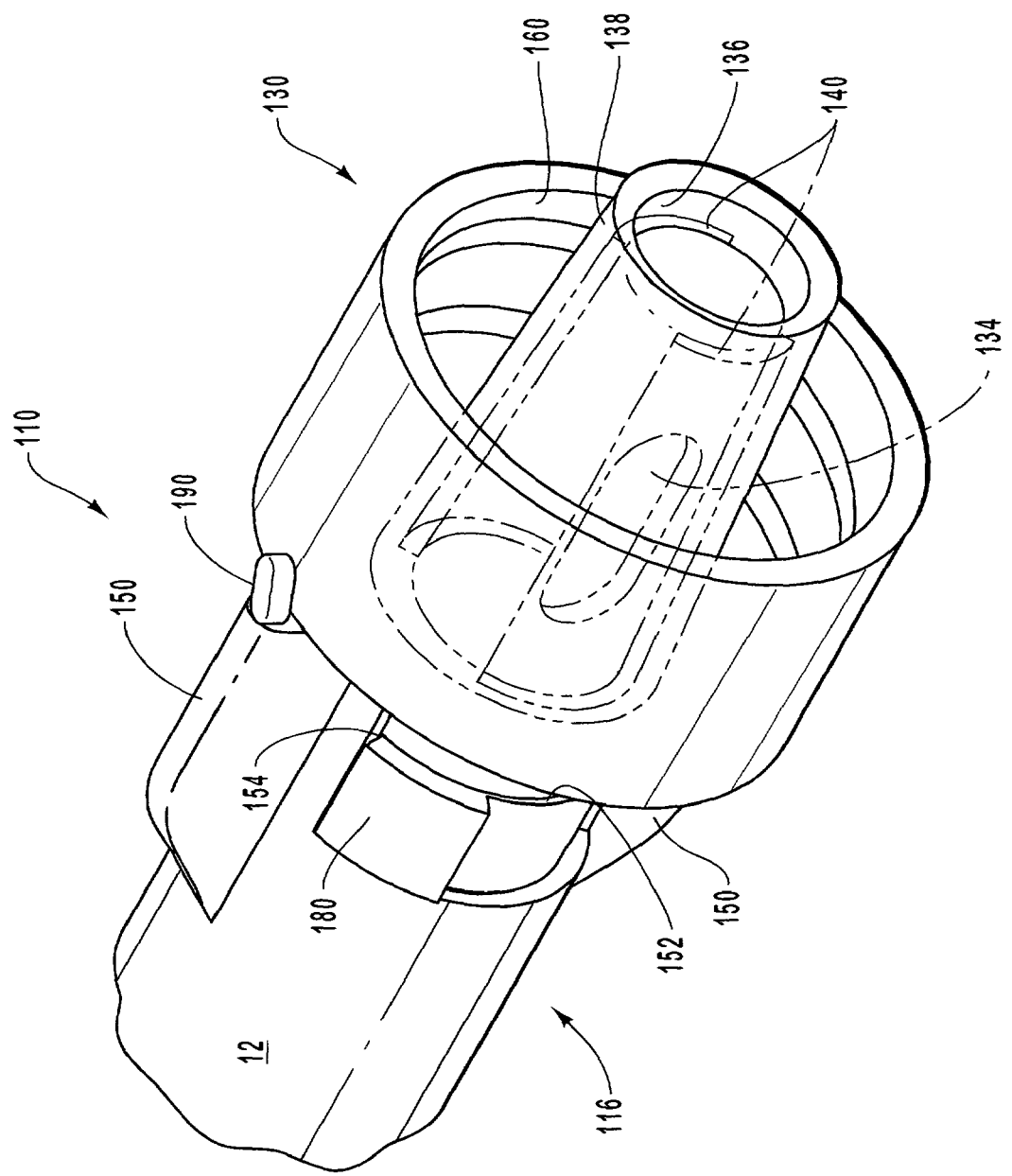
FIG. 8 illustrates one embodiment of the applicator valve of the invention that is disposed at the outlet end of the syringe barrel in an open rotational position and which includes threaded coupling means for coupling the applicator valve to a threaded applicator tip.

In one embodiment (not shown) the securing means is configured so as to prevent the applicator valve 10 from being removed at all. For instance, in this alternative embodiment, the securing means are configured internally, inside of the applicator valve 30, to prevent a user from removing the applicator valve 30 from the barrel 12. This embodiment may be preferred when the valve syringe is intended to be disposable, composed of an inexpensive material, and comprises only enough composition for a single FIGS. 7–9 illustrate an alternative embodiment of the valve syringe 110 of the invention in which the applicator valve 130 is configured with coupling means for coupling the applicator valve 130 to interchangeable applicator tips without removing the applicator valve 130 from the barrel 112 of the valve syringe 110. This embodiment is particularly useful for preventing premature curing in applicator tips between uses.

As shown in FIG. 7, similar to the previous embodiments, the applicator valve 130 includes a contact surface 136 that is configured to block the flow of the fluid material when the applicator valve 130 is in the closed position. As shown in FIG. 8, the applicator valve 130 also includes relief slots 140 that are configured to align with the barrel openings 134 (only one is shown) and to allow the fluid material to flow through the applicator valve 130 when the applicator valve 130 is rotated into the open position, as in the previous embodiments. The valve syringe 110 of the present embodiment also includes retaining means for retaining the applicator valve 130 on the outlet end 116 of the barrel 112. In particular, the valve syringe includes a ridge 152 and corresponding ledges 154 which, as generally described above, slidably engage in a suitable manner for retaining the applicator valve 130 on the outlet end 116 of the barrel 112.

One difference between the present embodiment and the previously disclosed embodiments, however, is that the applicator valve 130 includes a threaded surface 160 that circumferentially extends around the applicator valve 130 which is configured for threadably engaging and coupling with threaded applicator tips. This threaded surface 160 comprises one suitable coupling means for coupling the applicator valve 130 to interchangeable applicator tips. To accommodate industry standards, the internal mating surface 138 of the applicator valve 130 may be configured with a luer taper.

Figure 9A:
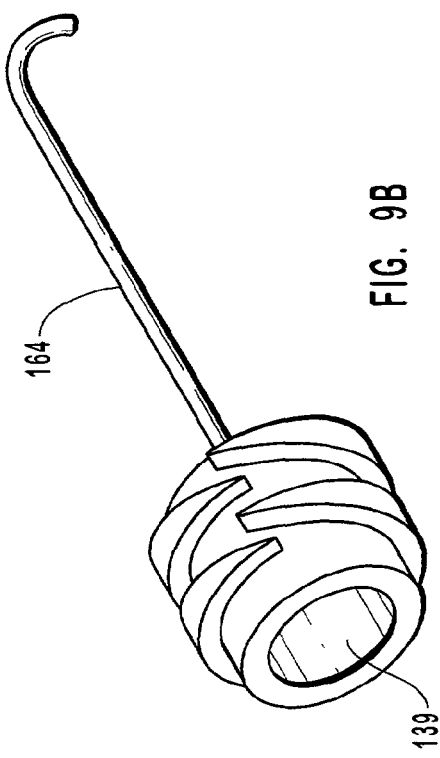
FIG. 9A illustrates a perspective view of one embodiment of the applicator tip of the invention which is threaded and configured as a needle.
Figure 9B:
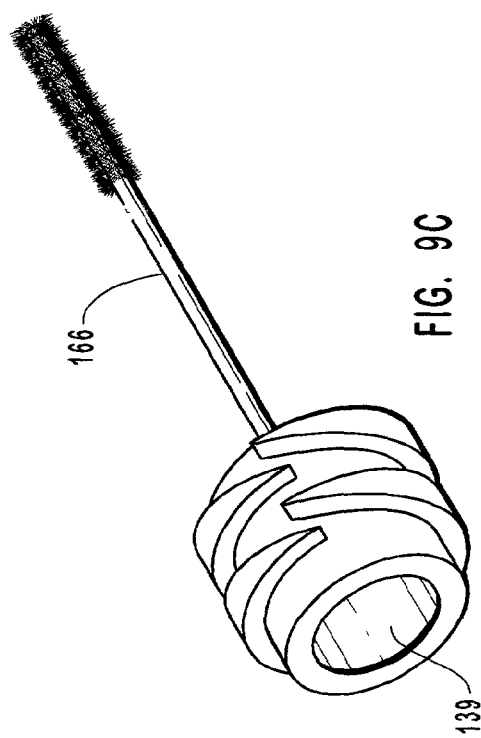
FIG. 9B illustrates a perspective view of one embodiment of the applicator tip of the invention which is threaded and configured as a curved cannula.
Figure 9C:
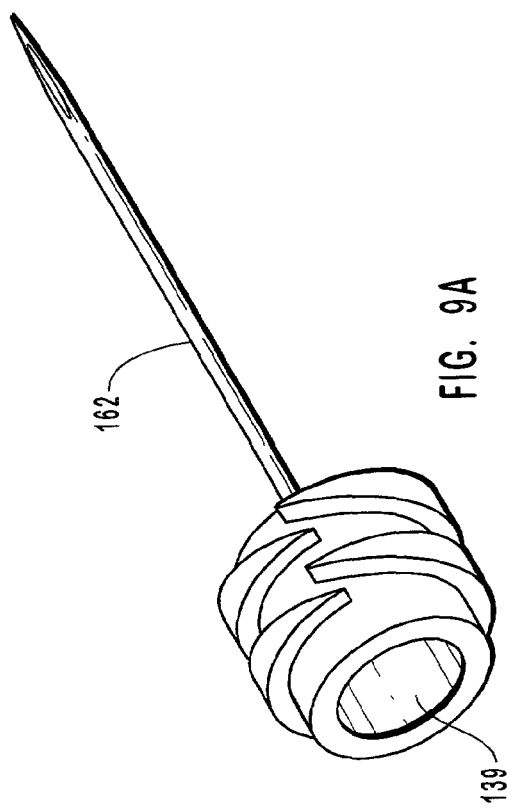
FIG. 9C illustrates a perspective view of one embodiment of the applicator tip of the invention which is threaded and includes a flocked surface.

As shown in FIGS. 9A–9C the applicator tips 162, 164, 166 can include a variety of different configurations, including, but not limited to a needle applicator 162, a curved cannula applicator 164, and a flocked applicator 166. It will be appreciated that the applicator tips can also include other embodiments which are not shown but which are suitably configured to couple with the applicator valve 130 and to dispense the composition contained in the valve syringe during use. The internal mating surface 139 of the applicator tips 162, 164, 166 is preferably configured in size and shape to frictionally engage the mating internal surface 138 of the applicator valve 130, described above.

Figure 10:
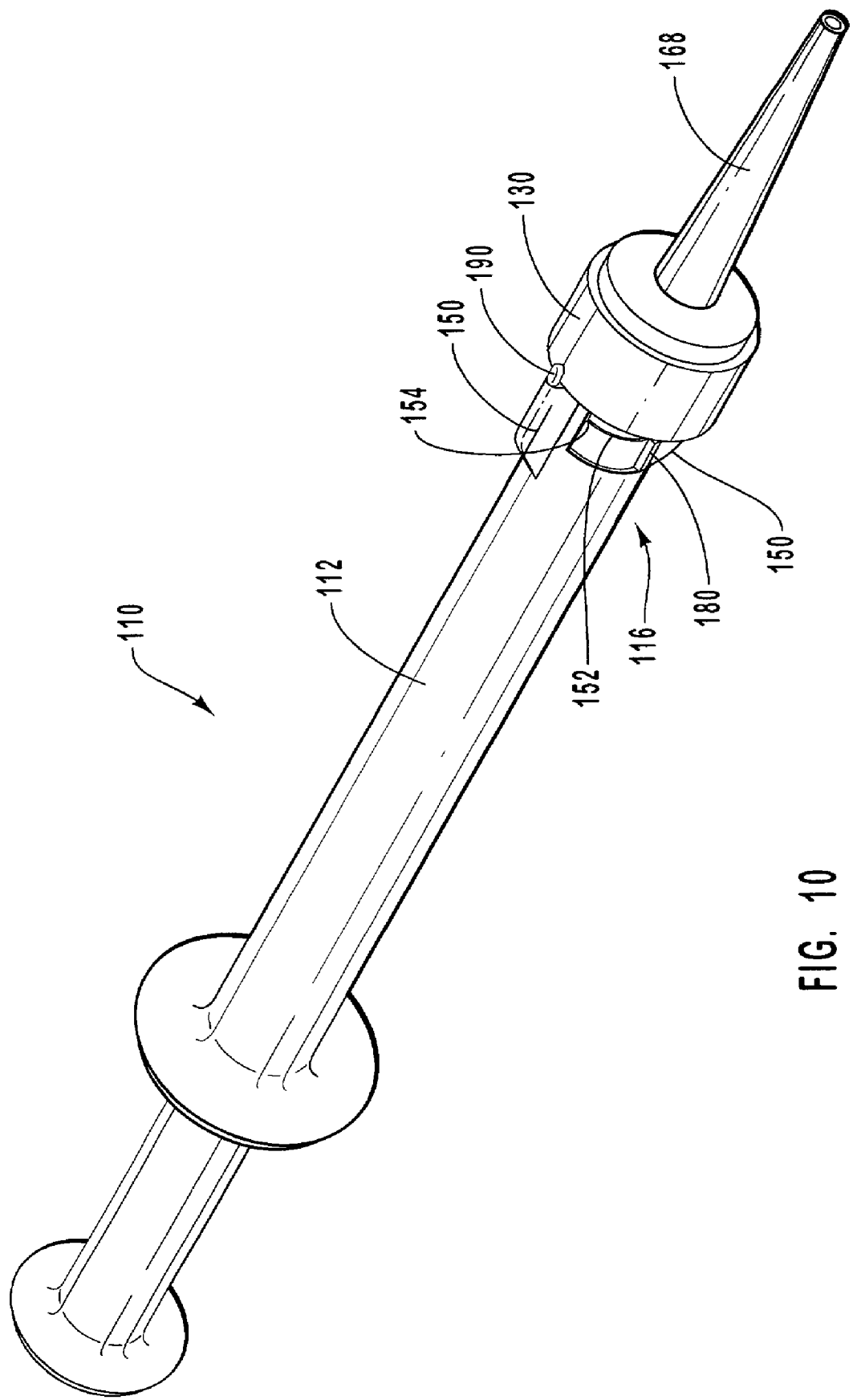
FIG. 10 illustrates a perspective view of one embodiment of the invention in which the valve syringe interconnects an applicator tip to the barrel of the syringe.

FIG. 10 illustrates one embodiment of the valve syringe 110 in which an applicator tip 168 is threadably coupled with the applicator valve 130. It will be appreciated that, as in the previous embodiments, the valve syringe 110 of the invention includes retaining means for retaining the applicator valve 130 on the outlet end 116 of the barrel 112. In particular, as shown in FIGS. 7 and 8, the valve syringe 110 includes tab members 150 with ledges 152, only one of which is shown, that are configured to engage the ridge member 154 circumferentially extending around the applicator valve 130. It will be appreciated that the valve syringe 110 may also include securing means comprising mating engagement formations, not shown, for releasably securing the applicator valve 130 in the closed position, as generally described above in reference to the knobs 42 and recesses 44 that are shown in FIG. 5.

The present embodiment is preferably configured to contain multiple doses of composition to be used over a period of time on a plurality of applications. This embodiment is useful, for instance, to maximize the cost efficiency of selling, shipping and storing the composition in bulk quantities. Inasmuch as the valve syringe 110 is intended for repeated use, it is useful to provide the valve syringe 110 with the coupling means that have been described for facilitating the ability to interchange the applicator tips between uses and to preserve a desired level of sanitation between uses.

According to other embodiments, as illustrated in FIGS. 1–5, the valve syringes 10 of the invention also include rotation facilitating means for facilitating rotation of applicator valve 30 between the closed and open positions. For instance, according to this embodiment, the valve syringes 10 comprise wing members 70 that extending from the applicator valve 30 and configured to be engaged by the fingers of a user. The wing members 70 enable a user to apply more leverage during rotation of the applicator valve 30. In another embodiment, not shown, the rotation facilitating means includes a frictional surface on the applicator valve 110. To prevent over-rotation of the applicator valve 30 and 130, the valve syringes 10 and 110 may also include stopping means for stopping rotation of the applicator valve 30 and 130 once the applicator valve 30 and 130 is sufficiently rotated into the open and closed positions. As shown in FIGS. 1–4, 6A–8 and 10, the stopping means may include one or more radial block members 80 and 180 protruding away from the applicator valves 30 and 130 which are configured to engage the tab members 50 and 150 once the applicator valves 30 and 130 are completely rotated into the open and closed positions.

In yet another embodiment, the valve syringes 10 and 110 of the invention include tamper evident means for indicating whether the applicator valve 30 and 130 has rotated from the closed position to the open position at least one time. For instance, as shown in FIGS. 1 and 3, bridge members 90 fixedly interconnecting the applicator valve 30 and the barrel 12 at the tab members 50 enables a user to visually determine whether the applicator valve 30 has been rotated out of the closed position. The bridge members 90 are noticeably and irreversibly broken, as shown in FIG. 4, when the applicator valve 30 is rotated from the closed position to the open position for the first time.

FIGS. 7–8 illustrate one alternative embodiment of how the tamper evident means can be used with the valve syringes of the invention. As shown, the tamper evident means includes a bridge member 190 that interconnect the applicator valve 130 and the barrel 112 at the general location of the tab member 150. According to this embodiment, the bridge member 190 is noticeably and irreversibly broken when the applicator valve 130 is rotated from the closed position to the open position for the first time. Despite the specific examples provided above, however, it should be appreciated that the tamper evident means can include any number of bridge members that interconnect any portions of the barrel 112 and the applicator valve 130 and are not, therefore, necessarily disposed at the general location of the tab members 50 and 150.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A valve syringe comprising:
   a barrel configured for containing a fluid material, the barrel including an inlet end and an outlet end, the outlet end including a sidewall with at least one barrel opening formed in the sidewall through which the fluid material can pass;
   at least one tab member integrally attached to the barrel, extending from the outlet end of the barrel, and spaced-apart from the sidewall so as to provide a space between the sidewall and the tab member;
   a plunger configured for pushing the fluid material contained in the barrel toward the outlet end of the barrel;
   an applicator valve disposed at the outlet end of the barrel and configured to rotate between an open position and a closed position, including:
      an internal contact surface configured to engage the outlet end of the barrel in a manner so as to prevent the fluid material from exiting through the at least one barrel opening when the applicator valve is in the closed position, and
      at least one relief slot formed in the internal contact surface and configured to allow the fluid material to pass through the barrel opening and into the at least one relief slot when the applicator valve is in the open position; and
   at least one ridge member integrally attached to the applicator valve and extending from the applicator valve on a side opposite the internal contact surface that engages the at least one tab member in order to retain the applicator valve at the outlet end of the barrel,
      wherein the at least one tab member is configured to slidably engage the at least one ridge member during rotation of the applicator valve between the open and closed position.

2. A valve syringe as recited in claim 1, further comprising mating engagement formations configured to mechanically or frictionally resist rotation of the applicator valve when the applicator valve is in the closed position.

3. A valve syringe as recited in claim 1, further comprising tamper evident means for indicating the applicator valve has rotated from the closed position to the open position at least one time.

4. A valve syringe as recited in claim 3, wherein the tamper evident means comprises a bridge member fixedly interconnecting the applicator valve and the barrel, such that said bridge member is noticeably and irreversibly broken when the applicator valve is rotated from the closed position to the open position for the first time.

5. A valve syringe as recited in claim 1, wherein the applicator valve further includes:
   an applicator tip configured to dispense the fluid material, and
   a hollow body configured to channel the fluid material passing into the at least one relief slot to the applicator tip.

6. A valve syringe as recited in claim 5, wherein the applicator tip comprises at least one of a cannula, a needle, a curved hollow body, and a flocked applicator tip.

7. A valve syringe as recited in claim 1, wherein the sidewall and the internal contact surface each comprise luer tapers.

8. A valve syringe as recited in claim 1, further comprising stopping means for stopping rotation of the applicator valve in the open position when the applicator valve is rotated in a first direction and for stopping rotation of the applicator valve in the closed position when the applicator valve is rotated in a second direction.

9. A valve syringe as recited in claim 8, wherein the stopping means comprises a radial block member protruding away from the applicator valve and configured to engage the at least one tab member when the applicator valve is completely rotated into either one of the open and closed positions.

10. A valve syringe as recited in claim 1, further comprising rotation facilitating means for facilitating rotation of the applicator valve between the open and closed positions.

11. A valve syringe as recited in claim 10, wherein the rotation facilitating means comprises at least one protruding wing member extending from the applicator valve and configured to be engaged by fingers of a user during rotation of the applicator valve.

12. A valve syringe comprising:
    a barrel configured for containing a fluid material, the barrel comprising an inlet end and an outlet end, wherein the outlet end includes a sidewall with at least one barrel opening formed in the sidewall through which the fluid material can pass;
    a plunger configured for pushing the fluid material contained in the barrel to the outlet end of the barrel;
    an applicator valve disposed at the outlet end of the barrel and configured to rotate between an open position and a closed position, including:
       an internal contact surface configured to engage the outlet end of the barrel and to prevent the fluid material from exiting through the at least one barrel opening when the applicator valve is in the closed position, and
       at least one relief slot formed in the internal contact surface, configured to allow the fluid material to pass through the barrel opening and into the at least one relief slot when the applicator valve is in the open position;
    coupling means for coupling the applicator valve to an applicator tip through which the fluid material is dispensed during use; and
    securing means for releasably securing the applicator valve in the closed position so as to resist rotation of the applicator valve toward the open position when the applicator valve is in the closed position.

13. A valve syringe as recited in claim 12, wherein the coupling means includes a threaded surface circumferentially extending around the applicator valve.

14. A valve syringe as recited in claim 12, wherein the applicator valve further comprises a coupling surface configured to seal the applicator valve with the applicator tip.

15. A valve syringe as recited in claim 14, wherein the coupling surface comprises a luer taper.

16. A valve syringe as recited in claim 12, wherein the securing means comprises mating engagement formations configured to frictionally resist rotation of the applicator valve only when the applicator valve is in the closed position.

17. A valve syringe comprising:
    a barrel configured for containing a fluid material, the barrel comprising an inlet end and an outlet end, wherein the outlet end includes a sidewall with at least one barrel opening formed in the sidewall through which the fluid material can pass;
    at least one tab member integrally attached to the barrel, extending from the outlet end of the barrel, and spaced-apart from the sidewall so as to provide a space between the sidewall and the tab member;

a plunger configured for pushing the fluid material contained in the barrel to the outlet end of the barrel;

a threadably detachable applicator tip configured to dispense the fluid material during use;

an applicator valve disposed at the outlet end of the barrel and configured to rotate between an open position and a closed position, including:
- an internal contact surface configured to engage the outlet end of the barrel and to prevent the fluid material from exiting through the at least one barrel opening when the applicator valve is in the closed position, and
- at least one relief slot formed in the internal contact surface, configured to allow the fluid material to pass through the barrel opening and into the applicator tip when the applicator valve is in the open position;

at least one ridge member integrally attached to the applicator valve and extending from the applicator valve on a side opposite the internal contact surface that engages the at least one tab member in order to retain the applicator valve at the outlet end of the barrel,
- wherein the at least one tab member is configured to slidably engage the at least one ridge member during rotation of the applicator valve between the open and closed position; and a threaded surface circumferentially extending around the applicator valve configured to detachably connect the applicator tip to the applicator valve.

18. A valve syringe as recited in claim 17, wherein the applicator valve is configured to be connected with at least one interchangeable applicator tip, and wherein each one of the applicator tip and the at least one interchangeable applicator tip comprise at least one of a cannula, needle, a curved applicator tip, and a flocked applicator tip.

19. A valve syringe comprising:

a barrel configured for containing a fluid material, the barrel including an inlet end and an outlet end, the outlet end including a sidewall with at least one barrel opening formed in the sidewall through which the fluid material can pass;

a plunger configured for pushing the fluid material contained in the barrel toward the outlet end of the barrel;

an applicator valve disposed at the outlet end of the barrel and configured to rotate between an open position and a closed position, including:
- an internal contact surface configured to engage the outlet end of the barrel in a manner so as to prevent the fluid material from exiting through the at least one barrel opening when the applicator valve is in the closed position, and
- at least one relief slot formed in the internal contact surface and configured to allow the fluid material to pass through the barrel opening and into the at least one relief slot when the applicator valve is in the open position;

tamper evident means for indicating the applicator valve has rotated from the closed position to the open position at least one time, the tamper evident means comprising a bridge member fixedly interconnecting the applicator valve and the barrel, such that said bridge member is noticeably and irreversibly broken when the applicator valve is rotated from the closed position to the open position for the first time; and securing means for releasably securing the applicator valve in the closed position so as to resist rotation of the applicator valve toward the open position when the applicator valve is in the closed position.

20. A valve syringe comprising:

a barrel configured for containing a fluid material, the barrel including an inlet end and an outlet end, the outlet end including a sidewall with at least one barrel opening formed in the sidewall through which the fluid material can pass;

a plunger configured for pushing the fluid material contained in the barrel toward the outlet end of the barrel;

an applicator valve disposed at the outlet end of the barrel and configured to rotate between an open position and a closed position, including:
- an internal contact surface configured to engage the outlet end of the barrel in a manner so as to prevent the fluid material from exiting through the at least one barrel opening when the applicator valve is in the closed position, and
- at least one relief slot formed in the internal contact surface and configured to allow the fluid material to pass through the barrel opening and into the at least one relief slot when the applicator valve is in the open position; and securing means for releasably securing the applicator valve in the closed postion so as to resist rotation of the applicator valve toward the open position when the applicator valve is in the closed position.

* * * * *

UNITED STATES PATENT AND TRADEMARK OFFICE
CERTIFICATE OF CORRECTION

PATENT NO. : 7,169,134 B2
APPLICATION NO. : 10/106397
DATED : January 30, 2007
INVENTOR(S) : Dan J. Bills Page 1 of 3

It is certified that error appears in the above-identified patent and that said Letters Patent is hereby corrected as shown below:

Drawings
Sheet 5, replace FIG. 5 with the figure provided below, wherein detail --34-- has been added

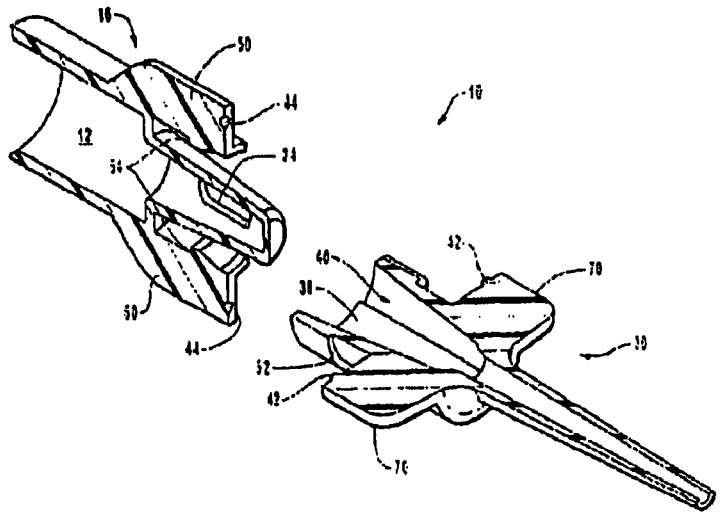

FIG. 5

Sheet 7, replace FIG. 7 with the figure provided below, wherein detail "12" has been changed to --112--

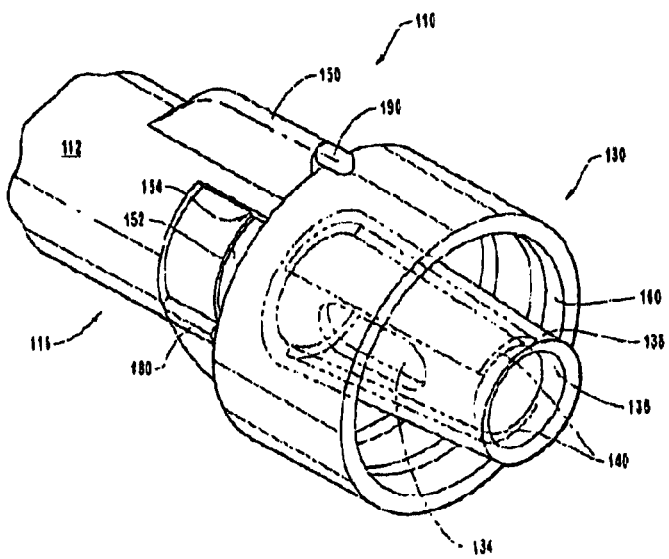

FIG. 7

UNITED STATES PATENT AND TRADEMARK OFFICE
CERTIFICATE OF CORRECTION

PATENT NO.         : 7,169,134 B2                                    Page 2 of 3
APPLICATION NO. : 10/106397
DATED              : January 30, 2007
INVENTOR(S)        : Dan J. Bills It is certified that error appears in the above-identified patent and that said Letters Patent is hereby corrected as shown below:

Sheet 8, replace FIG. 8 with the figure provided below, wherein detail "12" has been changed to --112--

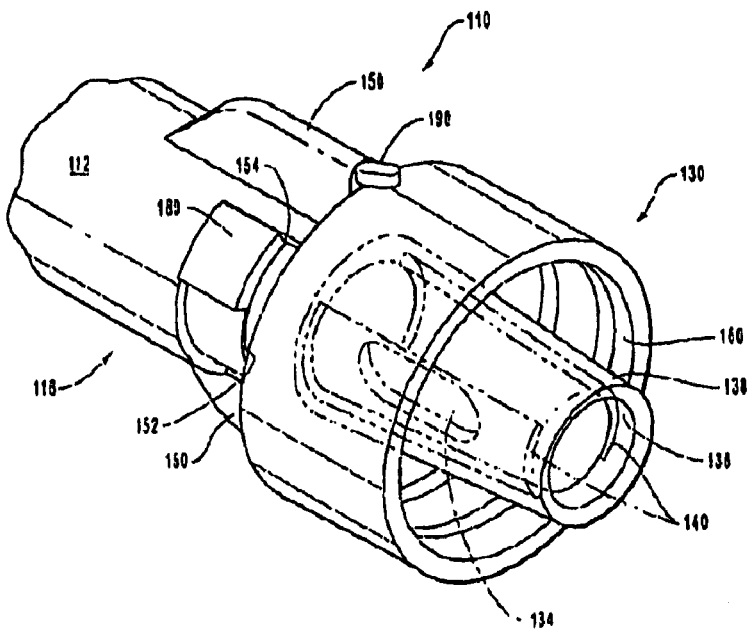

FIG. 8

Column 1
Line 48, before "syringe", remove --to--
Line 48, after "that", remove --that--

Column 2
Line 61, after "embodiment", add a comma --,--

UNITED STATES PATENT AND TRADEMARK OFFICE
CERTIFICATE OF CORRECTION

| | | |
|---|---|---|
| PATENT NO. | : 7,169,134 B2 | |
| APPLICATION NO. | : 10/106397 | |
| DATED | : January 30, 2007 | |
| INVENTOR(S) | : Dan J. Bills | |

It is certified that error appears in the above-identified patent and that said Letters Patent is hereby corrected as shown below:

Column 6
Line 44, after "such as", remove --may occur--

Column 7
Line 3, after "single", add --use.--

Signed and Sealed this

Second Day of September, 2008

JON W. DUDAS
*Director of the United States Patent and Trademark Office*